United States Patent
Feurer et al.

(10) Patent No.: US 6,274,535 B1
(45) Date of Patent: Aug. 14, 2001

(54) DEFOLIANT

(75) Inventors: Gerhard Feurer, Liederbach; Felix Thürwächter, Bad Homburg; Oswald Ort, Glashütten; Werner Schlesinger, Flörsheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/522,214

(22) Filed: Mar. 9, 2000

(30) Foreign Application Priority Data

Mar. 12, 1999 (DE) ................................. 199 11 165

(51) Int. Cl.⁷ ................... A01N 37/22; A01N 43/828; A01N 47/30; A01N 57/04
(52) U.S. Cl. ................... 504/128; 504/139; 504/165; 504/170
(58) Field of Search .................... 504/128, 139, 504/165, 170

(56) References Cited

U.S. PATENT DOCUMENTS 4,613,354   9/1986   Rusch ........................................ 71/73

FOREIGN PATENT DOCUMENTS 0 976 329 * 2/2000 (EP) .
1595148    7/1981 (GB) .

OTHER PUBLICATIONS

The Pesticides Manual, 11 ed., 170, 260, 281 and 703, 1997.

* cited by examiner

Primary Examiner—S. Mark Clardy
(74) Attorney, Agent, or Firm—Frommer Lawrence & Haug LLP

(57) ABSTRACT

A mixture comprising
 (A) thidiazoron or thidiazuron and diuron and
 (B) cyclanilide or cyclanilide and ethephon is suitable for effecting leaf abscission of plants, in particular in crops of cotton.

9 Claims, No Drawings

DEFOLIANT

The invention relates to the field of defoliants, in particular mixtures comprising thidiazuron and their use in crops of cotton.

Thidiazuron has been known for some time as a defoliant, in particular for use in crops of cotton (see, for example, "The Pesticide Manual", 11th edition, British Crop Protection Council, Farnham 1997).

The use of thidiazuron in mixtures has also been described, see, for example, DE-A 26 46 712.

However, since the economical and ecological demands placed on modern defoliants are constantly being increased, for example with respect to effect, application rate, residues, toxicity and favorable manufacturing, there is the permanent task of developing, for example by combining known active ingredients, novel defoliants which offer, at least in some areas, advantages compared with the known defoliants.

Surprisingly, it has now been found that thidiazuron and mixtures of thidiazuron and diuron which are already in commercial use have synergistic effects when mixed with cyclanilide or cyclanilide/ethephon.

The invention therefore provides a mixture, comprising
(A) thidiazuron or thidiazuron and diuron and
(B) cyclanilide or cyclanilide and ethephon.

The mixtures according to the invention are suitable in particular for use as defoliants in crops of cotton, for example by rapid and/or increased activity or reduced application rates. For the purposes of the invention, the term defoliant is synonymous with "desiccant" and also embraces the known growth-regulating effect of thidiazuron and of mixtures comprising thidiazuron.

The active ingredients (a.i.) used are known and commercially available, thidiazuron, cyclanilide and ethephon from Aventis Crop Science, France, and diuron from Griffin, USA.

The active ingredients, with specifications about their preparation, mixing and handling, are described, for example, in "The Pesticide Manual" (see above), under the following entry numbers: Thidiazuron 703, Diuron 260, Cyclanilide 170 and Ethephon 281.

Mixtures of thidiazuron and diuron are commercially available under the name Drop Ultra® (Aventis Crop Science, France). Such mixtures are described, for example, in U.S. Pat. No. 4,613,354.

The preferred component (A) is thidiazuron. The preferred component (B) is cyclanilide.

The combination of the active ingredients can be used in a manner which is customary per se, for example by spray application of a spray liquor prepared from individual formulations of the active ingredients in a tank mix or of a spray liquor prepared from a mixed formulation of the active ingredients by dilution with water. Methods which are suitable for the application are in particular those which are customary for the application of the individual active ingredients and which allow joint application.

In principle, application can also be carried out by successive applications of the individual active ingredients, where the possible interval can be determined in simple preliminary routine trials. However, preference is given to joint application. If appropriate, the active ingredients can also be used in combination with other active crop protection agents.

Having the same effect, the application rate of an individual active ingredient in the combination is considerably reduced compared with the application rate of the individual active ingredient in question when used on its own. The optimum choice of the ratio by weight and the application rates depends, for example, on the development stage, on environmental factors and climatic conditions or else on the type of the active crop protection agents which are additionally employed, if appropriate, and can be determined quickly by the person skilled in the art in simple routine trials.

The application rate of the component (A) is generally in the range from 1 to 500 g of active ingredient (=a.i.)/ha.

For thidiazuron, it is preferably in the range from 10 to 500 g of a.i./ha, particularly preferably from 10 to 300 g of a.i./ha, very particularly preferably from 20 to 200 g of a.i./ha, in particular from 20 to 150 g of a.i./ha.

In the case of thidiazuron/diuron mixtures (typically in a ratio by weight of 2:1), the application rate is generally in the range from 10 to 500 g of a.i./ha, preferably from 15 to 300 g of a.i./ha, particularly preferably from 20 to 200 g of a.i./ha, very particularly preferably from 30 to 200 g of a.i./ha, in particular from 30 to 150 g of a.i./ha.

The application rates of the component (B) can be varied within wide limits and are generally between 0.1 and 5000 g of a.i./ha.

Preferred application rates of the component (B) are, for example:

Cyclanilide:
From 40 to 400 g of a.i./ha, particularly preferably from 90 to 240 g of a.i./ha.

Cyclanilide/ethephon Mixture (typically 1:8):
From 500 to 4000 g of a.i./ha, particularly preferably from 800 to 2500 g of a. i./ha.

The ratios by weight of the components (A): (B) can vary within wide limits, they are usually between 1:100 and 100:1.

The approximate ratio (A): (B) is preferably
for cyclanilide 0.1–2:1, particularly preferably 1:2;
for cyclanilide/ethephon: 0.1–2:1.

The invention also provides defoliants, i.e. compositions for effecting leaf abscission of plants, comprising the combinations of the active ingredients (A) and (B) and customary formulation auxiliaries.

The combinations according to the invention and their individual active ingredients can be formulated in various ways, depending on the prevailing biological and/or chemico-physical parameters. Examples of possible suitable formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), granules (GR) in the form of microgranules, spray granules, coated granules and adsorption granules, water-dispersible granules (WG), water-soluble granules (SG), ULV (ultra-low-volume) formulations, microcapsules and WSBs (water-soluble bags).

These individual types of formulation are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other crop protection agents, such as, for example, insecticides, acaricides, herbicides, fungicides, safeners, other growth regulators and/or fertilizers, for example in the form of a ready mix or a tank mix.

Wettable powders are preparations which are uniformly dispersible in water and which, besides the active ingredient, also comprise ionic and/or nonionic surfactants (wetting agents, dispersants), for example polyethoxylated alkylphenols, polyethoxylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyltaurinate, in addition to a diluent or inert substance. To prepare the wettable powders, the active ingredients are ground finely, for example in customary equipment such as hammer mills, blower mills and air-jet mills, and simultaneously or subsequently mixed with the formulation auxiliaries.

Emulsifiable concentrates are prepared, by dissolving the active ingredients in an organic solvent, for example butanol, cyclohexanone, dimethylformamide, xylene, or else higher-boiling aromatics or hydrocarbons or mixtures of the organic solvents with the addition of one or more ionic and/or nonionic surfactants (emulsifiers). Examples of emulsifiers which can be used are: calcium salts of alkylarylsulfonic acid such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active ingredients with finely divided solid substances, for example talc, natural clays such as kaolin, bentonite and pyrophyllite, or diatomaceous earth. Suspension concentrates can be water- or oil-based. They can be prepared, for example, by wet grinding using commercially available bead mills with or without addition of surfactants as have already been mentioned above for example in the case of the other types of formulation.

Emulsions, for example oil-in-water emulsions (EW), can be prepared, for example, by means of stirrers, colloid mills and/or static mixers using aqueous organic solvents and, if appropriate, surfactants as have already been mentioned above for example in the case of the other types of formulation.

Granules can be prepared either by spraying the active ingredients onto adsorptive granulated inert material or by applying active ingredient concentrates to the surface of carriers such as sand, kaolinites or of granulated inert material by means of binders, for example polyvinyl alcohol, sodium polyacrylate or else mineral oils. The active ingredients can also be granulated in the manner which is conventional for the production of fertilizer granules.

Water-dispersible granules are generally prepared by the customary methodes such as spray-drying, fluidized-bed granulation, disk granulation, mixing with high-speed mixers and extrusion without solid inert material.

In general, the preparations according to the invention comprise 0.1 to 99% by weight, in particular 0.1 to 95% by weight, of active ingredients of the components (A) and (B).

The active ingredient concentration in wettable powders is, for example, approximately 10 to 90% by weight, the remainder to 100% by weight being composed of customary formulation components. In the case of emulsifiable concentrates, the active ingredient concentration may amount to approximately 1 to 90% by weight. Formulations in the form of dusts comprise, for example, 1 to 80% by weight of active ingredient, in most cases 5 to 60% by weight of active ingredient. Sprayable solutions comprise, for example, 0.05 to 80, in most cases 2 to 50, % by weight of active ingredients. The active ingredient content of water-dispersible granules depends partly on whether the active compound is in liquid or solid form and on which granulation auxiliaries, fillers and the like are being used. The active ingredient content of the water-dispersible granules amounts to, for example, between 1 and 95% by weight, in most cases between 10 and 80% by weight.

In addition, the abovementioned formulations of active ingredients comprise, if appropriate, adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can also be used in combination with the active ingredients according to the invention in mixed formulations or in the tank mix are, for example, known active ingredients as are described, for example, in Weed Research 26, 441–445 (1986), or "The Pesticide Manual", 11th edition, 1997, and the literature cited therein.

For use, the formulations, which are in commercially available form, are, if appropriate, diluted in the customary manner, for example using water in the case of wettable powders, emulsifiable concentrates, dispersions and water-dispersible granules, and then applied to the plants. This includes specific application variants customary in particular in cotton cultivation, for example the application by aeroplane. Preparations in the form of dusts, granules for soil application or for broadcasting and also sprayable solutions are conventionally not diluted any further with other inert substances prior to use.

The invention also provides the use of the compositions or mixtures according to the invention as defoliant, i.e. for effecting leaf abscission of plants, preferably in suitable crops of useful plants, such as cotton, sunflowers or potatoes. Particular preference is given to the use as defoliant in crops of cotton.

The invention likewise provides a method for effecting leaf abscission of a plant, preferably a useful plant, particularly preferably a cotton plant, which comprises treating the plant with a mixture according to the invention or a composition according to the invention.

The mixtures or compositions and the method can, of course, also be employed for treating genetically modified (transgenic) plants, preferably useful plants, particularly preferably cotton plants, where such plants contain, for example, one or more foreign genes in order to obtain resistance against insecticides and/or herbicides.

The content of the German Patent Application 199 11 165.0 and the enclosed Abstract are hereby incorporated by reference into the present description.

The invention is illustrated in more detail by the examples without being limited thereby.

EXAMPLES

1. Assessment of the Effect and Evaluation of the Synergism

The effect on the plants is evaluated by leaf abscission according to a scale from 0 to 100%:

0%=no noticeable effect when compared with the untreated plant;

100%=all leaves have been dropped.

When assessing the synergism between the active ingredients employed here, the highly different application rates of the individual active ingredients have to be taken into consideration. Thus, it is not expedient to compare the effects of the active ingredient combinations with those of the individual active ingredients in each case at identical application rates. The amounts of active ingredients that can be saved according to the invention become evident from the superadditive increase in activity when using the combined application rates or by the reduction of the application rates of the two individual active ingredients in the combination in comparison to the application rates of the active ingredients applied on their own, the activity remaining the same in each case.

In all instances, a distinction is made in the combinations between the calculated degree of action and the degree of action found. In most cases, the synergistic increase in activity is so high that the activity of the combination considerably surpasses the formal (calculated) total of the activities of the individual ingredients. Such a greatly increased activity was not to be expected based on the known activities of the individual active ingredients.

The expected theoretical degree of action of a combination can be approximately estimated by the formula of S. R. Colby (cf. "Calculation of synergistic and antagonistic responses of herbicide combinations", Weeds 15 (1967), pages 20–22).

For combinations of two compounds, this formula is:

$$E = X + Y - \frac{X \cdot Y}{100}$$

where

X=% activity by A at an application rate of x kg/ha;

Y=% activity by B at an application rate of y kg/ha;

E=expected activity by A+B at x+y kg/ha

If the observed activity exceeds the calculated expected activity, the activity of the combination is more than additive, i.e. there is a synergistic effect.

2. Action as Defoliant

2.1. General Procedure

Cotton seeds of the variety Vulkano were sown at a depth of 1 cm and grown in a climatized chamber (14 h of light, temperature during the day: 25° C., at night: 18° C.) until they had reached the 8–10 leaf stage.

2.2. Table 1 (Mixtures with cyclanilide)

Application was carried out using an overhead laboratory sprayer with a Teejet 11002XR nozzle, in an amount of 300 l/ha.

| No. | Active ingredient (combination) | Dose g/ha | Effect in % | | |
|---|---|---|---|---|---|
| | | | 5 days | 10 days | 15 days |
| 1. | Thidiazuron* (TDZ) | 80 | 23 | 38 | 65 |
| 2. | Thidiazuron | 60 | 23 | 45 | 45 |
| 3. | Cyclanilide (Cyd.) | 160 | — | — | — |
| 4. | TDZ + Cycl. | 80 + 160 | 60 | 83 | 78 |
| 5. | TDZ + Cycl. | 60 + 160 | 40 | 75 | 70 |
| 6. | TDZ + Diuron (Diu.)** | 36 + 18 | 8 | 45 | 70 |
| 7. | TDZ + Diu. | 60 + 30 | 23 | 95 | 100 |
| 8. | TDZ + Diu. + Cydl. | 36 + 18 + 100 | 30 | 75 | 80 |
| 9. | TDZ + Diu. + Cycl. | 60 + 30 + 160 | 60 | 95 | 100 |

*Drop ® WP
**Drop Ultra ® SC

These experiments demonstrate a significant synergism.

What is claimed is:

1. A mixture, consisting of (A) thidiazuron or thidiazuron and diuron and (B) cyclanilide.

2. The mixture as claimed in claim 1, wherein the component (A) is thidiazuron.

3. A defoliant consisting of (A) thidiazuron or thidiazuron and diuron, (B) cyclanilide and (C) one or more formulation auxiliares.

4. A method for effecting leaf abscission of plants, which comprises treating the plant with a mixture as claimed in claim 1.

5. A method for effecting leaf abscission of plants, which comprises treating the plant with a defoliant as claimed in claim 3.

6. The method as claimed in claim 4, wherein the plant is a cotton plant.

7. The method as claimed in claim 5, wherein the plant is a cotton plant.

8. The method as claimed in claim 6, wherein the plant is a cotton plant.

9. The method as claimed in claim 7, wherein the cotton plant is a transgenic cotton plant.

* * * * *